United States Patent [19]
Baldenius et al.

[11] Patent Number: 6,096,907
[45] Date of Patent: Aug. 1, 2000

[54] PROCESS FOR PREPARING CHROMANOL DERIVATIVES

[75] Inventors: Kai-Uwe Baldenius, Frankenthal; Bernhard Bockstiegel, Römerberg; Hagen Jaedicke; Detlef Ruff, both of Ludwigshafen; Carsten Siedenbiedel, Mannheim; Rainer Stürmer, Rödersheim-Gronau, all of Germany

[73] Assignee: BASF Aktiengesellscahft, Ludwigshafen, Germany

[21] Appl. No.: 09/395,774

[22] Filed: Sep. 14, 1999

[30] Foreign Application Priority Data

Sep. 23, 1998 [DE] Germany ............ 198 43 672

[51] Int. Cl.[7] .................................................. C07D 311/76
[52] U.S. Cl. .................. 549/408; 549/410; 549/412
[58] Field of Search .................... 549/406, 408, 549/410, 412

[56] References Cited

PUBLICATIONS

Karrer et al., *Helv. Chim. Acta*, 27, 1944, p. 1297–1300.
Kabbe et al., *Angew. Chem. Int. Ed. Engl.*, 21, 1982, 247–256.
Von Schudel et al., *Helv. Chim. Acta*, 46, 1963, 2517–2526.
Kabbe, *Synthesis*, 1978, 886–889.
Pearce et al., *J. Med. Chem.*, 37, 1994, 526–541.
*Ullmann's Enc. of Ind. Chem.*, 5th Ed., vol. A27, 1996, 484–485.
Read et al., *Org. Synth.*, Coll. vol. 3, 1955, 444–46.
Bramwell et al, *J. Chem. Soc.*, 1965, 3882–84.
Anderson et al., *J. Biol. Chem.*, 127, 1939, 649–656.
Dann et al., *Justus Liebigs Ann. Chem.*, 587, 1954, 16–37.
Bridge et al., *J. Chem. Soc.*, 1937, 1530–35.
Urano et al., *Chem. Pharm. Bull.*, 31(12), 1983, 4341–45.
Pigini et al., *J. Med. Chem.*, 31(12), 1988, 2300–04.
Robertson et al., *J. Chem. Soc.*, 1950, 3117–23.
Robertson et al., *J. Chem. Soc.*, 1937, 286–92.
Cimino et al., *Tetrahedron*, 41(6), 1985, 1093–1100.
Banfield et al., *Aust. J. Chem.*, 47(4), 1994, 587–608.
Zakharova et al., *Pharm. Chem. J.*, 19(9), 1985, 614–16.

*Primary Examiner*—Amelia Owens
*Attorney, Agent, or Firm*—Keil & Weinkauf

[57] ABSTRACT

A process for preparing chromanol derivatives of the formula I

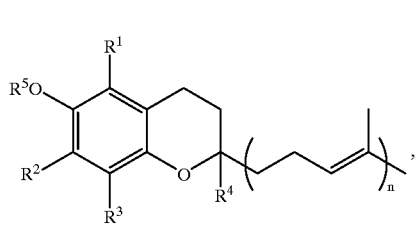

(I)

where
n is from 1 to 10,
$R^1, R^2,$
$R^3, R^4$ independently of one another are hydrogen or $C_1-C_4$ alkyl,
$R^5$ is hydrogen, $C_1-C_4$ alkyl, $C_6-C_{10}$ aryl, $C_7-C_{18}$ aralkyl, $C_7-C_{18}$ alkylaryl, $C_1-C_{22}$ acyl, or a group protecting the hydroxyl,
by reduction of the corresponding 4-oxochromanol derivatives of the formula II

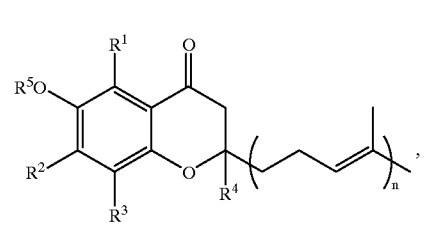

(II)

comprises reacting the 4-oxochromanol derivatives of the formula II with metallic zinc in the presence of an acid or an acid mixture.

Compounds of the formula I having $C_1-C_{22}$ acyl as radical $R^5$ can also be prepared by the above-described reduction of the compounds of the formula II with hydrogen as radical $R^5$ and simultaneous or subsequent esterification.

8 Claims, No Drawings

PROCESS FOR PREPARING CHROMANOL DERIVATIVES

The invention relates to a process for preparing chromanol derivatives having olefinic side chains by reduction of the corresponding 4-oxochromanol derivatives.

Chromanols having isoprenoid side chains, such as the tocopherol and tocotrienol group, show vitamin E activity and are therefore of importance as active biological ingredients. However, preparing chromanol derivatives having olefinic isoprenoid side chains such as tocotrienol is complex, since the acidic synthesis conditions which are usual, for example, in the preparation of tocopherol (Ullmann's 5th Ed 1996, Vol. A27, Chapter 4.11.2, pp. 484–485) lead to isomerization or cyclization of the olefinic side chain (P. Karrer, H. Reutschler, Helv. Chim. Acta 27, (1944) 1297; H. J. Kabbe, A. Widdig, Angew. Chem. Int. Ed. Engl. 21, (1982) 247–256, P. Schudel, H. Mayer, J. Metzger, R. Rüegg, O. Isler, Helv. Chim. Acta 46, (1963) 2517).

It is known to prepare tocotrienols by reduction of the corresponding 4-oxotocotrienols, which can be synthesized by a process known per se (H. J. Kabbe, A. Widdig, Angew. Chem. Int. Ed. Engl. 21, (1982) 247–256; H. J. Kabbe, H. Heitzer, Synthesis (1978) 888).

It is known to carry out the reduction in a multistage process, using sodium boranate to give 4-hydroxytocotrienol, subsequent water elimination by distillation and further partial hydrogenation using Na/ethanol (H. J. Kabbe, H. Heitzer, Synthesis (1978) 888). Owing to the multistage process, this process is highly complex.

It is further known to carry out the reduction in a single-stage process by using complex aluminum hydrides (B. C. Pearce et al., J. Med. Chem. 37, (1994) 526–541). Use of the complex hydrides on an industrial scale is uneconomic and requires particularly stringent safety precautions.

It is an object of the present invention, therefore, to remedy the defects described and develop a simple single-stage reduction process to reduce the 4-oxochromanols having an olefinic, isoprenoid side chain to give the corresponding chromanol derivatives without changing the double bond geometry or position in the unsaturated side chain by isomerization or cyclization.

We have found that this object is achieved by a process for preparing chromanol derivatives of the formula I

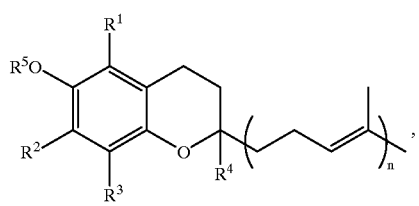

(I)

where n is from 1 to 10, $R^1$, $R^2$, $R^3$, $R^4$ independently of one another are hydrogen or $C_1$–$C_4$ alkyl and $R^5$ is hydrogen, $C_1$–$C_4$ alkyl, $C_6$–$C_{10}$ aryl, $C_7$–$C_{18}$ aralkyl, $C_7$–$C_{18}$ alkylaryl, $C_1$–$C_{22}$ acyl, or a group protecting the hydroxyl, by reduction of the corresponding 4-oxochromanol derivatives of the formula II

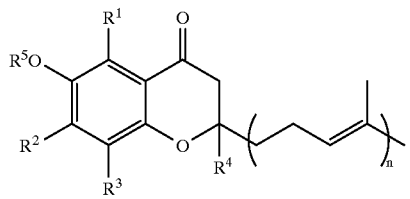

(II)

by reacting the 4-oxochromanol derivatives with metallic zinc in the presence of an acid or an acid mixture.

The Clemmensen reduction which is known per se (R. R. Read et al, Org. Synth. Collect. Vol. 3, (1955) 444; P. S. Bramwell, J. Chem. Soc. (1965) 3882) has not previously been considered for achieving the object, since the acidic reaction conditions which are usual for the Clemmensen reduction are not compatible with the acid-labile olefinic side chain (H. J. Kabbe, H. Heitzer, Synthesis (1978) 888). It has been found that, using the process according to the invention, 4-oxochromanols having an unsaturated side chain can be successfully reduced without the olefinic side chain isomerizing or cyclizing.

Starting materials of the process are the 4-oxochromanol derivatives of the formula II. The olefinic, isoprenoid side chain can consist of one to ten isoprene units (n=1 to 10).

Preferred starting materials are 4-oxochromanol derivatives having n=2 to 4 isoprene units, particularly preferably the group consisting of the 4-oxotocotrienols having n=3 isoprene units.

The radicals $R^1$, $R^2$, $R^3$ and $R^4$ can be here, independently of one another, hydrogen or $C_1$–$C_4$ alkyl such as methyl, ethyl, n-propyl, isopropyl, n-butyl, isobutyl or t-butyl, hydrogen and methyl being preferred.

$R^5$ is hydrogen, $C_1$–$C_4$ alkyl as described above, $C_6$–$C_{10}$ aryl such as phenyl, $C_7$–$C_{18}$ aralkyl such as benzyl, phenylethyl, $C_7$–$C_{18}$ alkylaryl such as tolyl, mesityl, or $C_1$–$C_{22}$ acyl such as $C_1$–$C_{22}$ alkylacyl, in particular formate, acetate, propionate, butyrater pentanoate, hexanoate, heptanoate, 2-ethylhexanoate, octanoate, nonanoate, decanoate, undecanoate, laurate, palmitate or stearate, or such as an olefinic $C_2$–$C_{22}$ acyl, in particular acrylate, methacrylate, crotonate, sorbate, 9-octadecenoate, linolate, linolenate, eicosapentaenoate or docosahexaenoate.

In addition, $R^5$ can be a usual hydroxyl-protecting group. To carry out the process according to the invention, the presence of a protecting group is not critical, but also does not interfere. The protecting group can be introduced first in the process according to the invention as an additional process step. For the case where $R^5$= hydrogen, the protecting group can be introduced simultaneously or as an additional step subsequently to the process according to the invention. In principle, any protecting group can be used. Preferred protecting groups are those known in the literature for hydroxyl groups (T. W. Greene, Protective Groups in Organic Synthesis, John Wiley & Sons New York, (1981), pages 14–71; P. J. Kocienski, Protecting Groups, Georg Thieme Verlag Stuttgart, (1994), pages 21–94). Examples of protecting groups are:

Esters, such as acetate (Ac), monochloro- to trichloroacetate, trifluoroacetate, phenylacetates, triphenylmethoxyacetate, phenoxyacetates, halophenoxyacetates, haloalkylphenoxyacetates, formate, benzoyl formate, 3-phenylpropionate, isobutyrate, pivaloate (Pv), adamantoate, crotonates, benzoates.

Silyl ethers, such as trimethylsilyl (TMS), triethylsilyl (TES), methyldi-t-butylsilyl, tert-butyldimethylsilyl (TBS or TBDMS), tert-butyldiphenylsilyl (TBDPS), triphenylsilyl, triisopropylsilyls (TIPS), diethylisopropylsilyl (DEIPS), isopropyldimethylsilyl (IPDMS), thexyldimethylsilyl (TDS).

aliphatic and aromatic ethers, such as methyl (Me), benzyl (Bn), o-nitrobenzyl, p-methoxybenzyls, 3,4-dimethoxybenzylether, trityls (Trt or Tr), p-methoxyphenyldiphenylmethyl (MMTr), 4,4', 4"-tris(benzoyloxy)trityl (TBTr), di(p-methoxyphenyl) phenylmethyl (DMTr), tert-butyls, 9-phenyl-9-xanthenyl (pixyl), allyls, 2-(trimethylsilyl)ethyl (TMSE).

Acetals (alkoxyalkyl ethers, aryloxyalkyl ethers or alkyloxyaryl ethers), such as methoxymethyl (MOM), methylthiomethyl (MTM), 2-methoxyethoxymethyl (MEM), 1-methoxy-1-methylethyl, 2-ethoxyethyl (EE), 4-methoxytetrahydropyran-4-yl (MTHP), tetrahydropyran-2-yl, 2-(trimethylsilyl)ethoxymethyl (SEM), 3,4-dimethoxybenzyl (DMB), benzyloxymethyl, p-methoxybenzyl (PMB), p-methoxybenzyloxymethyl (PMBM) and methoxycarbonyls and allyloxycarbonyls (Alloc), and protecting groups derived from these which may be non-alkylated or alkylated or non-halogenated or halogenated.

Particularly preferred starting materials are the 4-oxotocotrienols ($R^5$=hydrogen, n=3) such as 4-oxo-α-tocotrienol ($R^1=R^2=R^3=R^4$=methyl),
4-oxo-β-tocotrienol ($R^1=R^3=R^4$=methyl, $R^2$=hydrogen)
4-oxo-γ-tocotrienol ($R^1$=hydrogen, $R^2=R^3=R^4$=methyl) or
4-oxo-δ-tocotrienol ($R^1=R^2$=hydrogen, $R^3=R^4$=methyl)
4-oxo-tocotrienol ($R^1=R^2=R^3$=hydrogen, $R^4$=methyl)
4-oxo-2-desmethyltocotrienol ($R^1=R^2=R^3=R^4$=hydrogen)

and the corresponding compounds which are protected at the oxygen ($R^5$=protecting groups mentioned above) or derivatized at the oxygen ($R^5=C_1-C_4$ alkyl, $C_6-C_{10}$ aryl, $C_7-C_{18}$ aralkyl, $C_7-C_{18}$ alkylaryl or $C_1-C_{22}$ acyl).

The 4-oxochromanol derivatives are reduced according to the invention with metallic zinc in the presence of an acid or an acid mixture to the corresponding chromanol derivatives of the formula I.

Acids are taken to mean Brönsted acids and their aqueous solutions. Preferred Brönsted acids are mineral acids, such as hydrohalic acids, sulfur acids, nitric acid, phosphorus acids, boric acid or oxy-halogen acids, in particular HCl, HBr, HI, HF, $H_2SO_4$, methanesulfonic acid, $KHSO_4$, $HNO_3$, $HClO_4$, $H_3PO_4$ and $H_3BO_3$ or nonhalogenated or halogenated $C_1-C_{22}$ alkanecarboxylic acids, i.e. unsubstituted or independently of one another substituted by up to 5 halogens such as F, Cl or Br, such as formic acid, acetic acid, trifluoroacetic acid, propionic acid, butyric acid, citric acid, oxalic acid, hexanoic acid, octanoic acid, decanoic acid (capric acid), dodecanoic acid (lauric acid), hexadecanoic acid (palmitic acid) or octadecanoic acid (stearic acid).

In the case of the aqueous solutions, the amount of the Brönsted acid in the aqueous solution when use is made of mineral acids is preferably from 5 to 80% by weight, particularly preferably from 15 to 50% by weight, when use is made of aliphatic or aromatic $C_1-C_{22}$ carboxylic acids preferably from 10 to 80% by weight, particularly preferably from 35 to 50% by weight. Use can also be made of mixtures of the abovementioned acids.

The amount of metallic Zn powder added is typically from 1 to 25 molar equivalents, in particular from 1 to 10 molar equivalents, based on the amount of the 4-oxochromanol derivative. The reaction temperature is preferably from 0 to 160° C., in particular from 20 to 100° C. The reaction period is typically from 10 min to 24 h.

In a preferred embodiment, the reaction mixture of starting material (4-oxochromanol derivative), zinc and acid is admixed with an organic solvent. This can produce a multiphase mixture. For the purposes of the invention, organic solvents are aliphatic and aromatic hydrocarbons, such as cyclohexane, hexane, heptane, octane, nonane, benzene, toluene, xylene or ethylbenzene, alcohols, such as octanol, 2-ethylhexanol or nonylphenol, ethers, such as dibutyl ether or tert-butyl methyl ether or $C_1-C_{22}$ carboxylic acids, such as hexanoic acid, octanoic acid or decanoic acid. A mixture of these can also be used as organic solvent.

When an organic solvent is added, the use of an aqueous hydrohalic acid solution as acid is preferred. Particular preference is given to the use of an aqueous HCl solution (hydrochloric acid solution).

In addition, in a further embodiment, the reaction mixture can be admixed with a surface-active or phase-transfer-active substance, such as dodecyl sulfate, dodecylamine or dodecylammonium chloride, tridecylamine or tridecylammonium chloride, methyltrioctylammonium chloride, benzyltrimethylammonium bromide or tetraphenylphosphonium bromide. Further additives which can advantageously be admixed are, in particular, halide salts, such as lithium chloride, sodium chloride, magnesium chloride, potassium bromide, cesium fluoride or tetramethylammonium chloride. Advantageously, the process can be carried out under ultrasound.

In a further preferred embodiment, the $C_1-C_{22}$ alkanecarboxylic acids which are used as Brönsted acids can themselves serve as solvent. In this case, the 4-oxochromanol derivatives of the formula II are reacted with zinc in a $C_1-C_{22}$ alkanecarboxylic acid, as mentioned above, without additional admixing of an organic solvent. Preferred acids of this embodiment are formic acid, acetic acid, propionic acid, butyric acid, pentanoic acid, hexanoic acid, heptanoic acid, octanoic acid, decanoic acid, dodecanoic acid, palmitic acid or stearic acid. Particular preference is given to the use of acetic acid.

As described above, the step of introducing a protecting group or derivatizing the hydroxyl ($R^5$) can also be carried out simultaneously or subsequently to the process according to the invention. Preference is given in this case to introducing an ester group, owing to the pharmacological relevance.

For preparing chromanol esters of the formula Ia

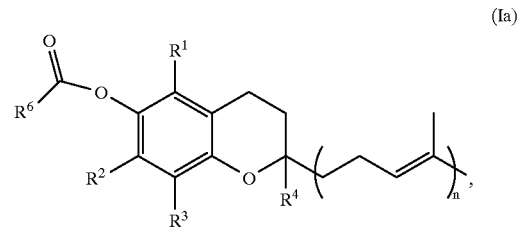

(Ia)

where $R^1$, $R^2$, $R^3$, $R^4$ and n have the meanings described above and $R^6$ is hydrogen, $C_1-C_{21}$ alkyl, such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl or heneicosyl or $C_2-C_{21}$ alkenyl, such as ethenyl, 1-propenyl, 2-propenyl, 8-heptadecenyl, 8,11-heptadecadienyl or 8,11,14-heptadecatrienyl, an overall process can therefore be carried out, which comprises preparing the chromanol derivatives of the formula I where $R^5$=hydrogen (Ib)

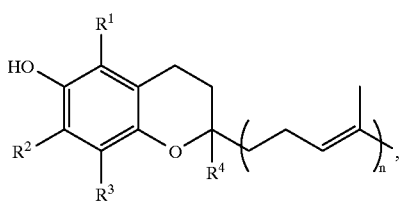

(Ib)

by the process according to the invention by reduction of the corresponding 4-oxochromanol derivative of the formula II ($R^5$=hydrogen) and esterifying this in a usual manner by reacting it with an aliphatic $C_1$–$C_{22}$ carboxylic acid derivative of the formula III $$R^6\text{-COX} \qquad (III),$$

where

X is a leaving group which can be displaced by the hydroxyl of the chromanol derivative of the formula Ib.

The esterification is therefore performed in a manner known per se by reacting the chromanol derivative of the formula Ib with $C_1$–$C_{22}$ alkanecarboxylic acids ($R^6$=$C_1$–$C_{21}$ alkyl, X=OH) as described as Brönsted acids above, $C_2$–$C_{22}$ alkenecarboxylic acids ($R^6$=$C_2$–$C_{21}$ alkenyl, X=OH), such as acrylic acid, methacrylic acid, crotonic acid, sorbic acid, oleic acid, linoleic acid, linolenic acid, eicosapentaenoic acid or docosahexaenoic acid, or with the corresponding aliphatic $C_1$–$C_{22}$ carboxylic acid derivatives (esterifying agents), i.e. the corresponding $C_1$–$C_{22}$ alkanecarboxylic acid derivatives or $C_2$–$C_{22}$ alkenecarboxylic acid derivatives. The aliphatic $C_1$–$C_{22}$ carboxylic acid derivatives of the formula III comprise carboxylic anhydrides, carboxylic acid halides, such as carboxylic acid chlorides, fluorides or bromides or carboxylic-active esters of $C_1$–$C_{22}$ alkanecarboxylic acids or $C_2$–$C_{22}$ alkenecarboxylic acids.

Examples of carboxylic-active esters are carboxylic esters such as carboxylic esters of N-hydroxysuccinimide, phenol esters and halophenol esters such as pentafluorophenol esters and trichlorophenol esters.

Examples of the leaving group X are correspondingly halides such as F⁻, Cl⁻, Br⁻, carboxylates such as acetate or propionate or alkoxides such as succinimide-N-hydroxylate, phenolate, halophenolates such as pentafluorophenolate, trichlorophenolates or benzotriazole-1-hydroxylate.

Preferred esterifying agents are acetylation agents such as acetic anhydride or acetyl chloride.

In a preferred embodiment, for preparing chromanol $C_1$–$C_{22}$ alkanecarboxylic esters, the chromanol derivatives of the formula I where $R^5$=hydrogen (Ib) are prepared by the process according to the invention using $C_1$–$C_{22}$ alkanecarboxylic acids as Brönsted acids or organic solvent, use being made of these $C_1$–$C_{22}$ alkanecarboxylic acids simultaneously, advantageously in situ, as esterifying agent.

The process according to the invention serves for simplified synthesis of chromanol derivatives by reduction of the corresponding 4-oxochromanol derivatives. Compared with the prior art, it is distinguished by the following advantages:

The process can be carried out simply, in one process step.

The process, even on an industrial scale, does not require stringent safety precautions.

The process requires starting materials which are readily available industrially and are inexpensive.

The examples illustrate the invention

EXAMPLES 1 to 6

Preparation of γ-tocotrienol by reduction of 4-oxo-γ-tocotrienol in n-heptane with Zn and an aqueous HCl solution The experimental results summarized in Tables 1 and 2 were achieved in correspondence with the experimental conditions below.

4-Oxo-γ-tocotrienol (from 1 g to 10.3 g, from 2.36 mmol to 24 mmol) was dissolved by warming in n-heptane (Examples 1–4), toluene (Example 5) or octanoic acid (Example 6). After cooling this solution to room temperature, an aqueous HCl solution (from 20 to 24% by weight, based on the aqueous solution) was added with stirring. In the course of 10 minutes, zinc powder (5 or 10 molar equivalents (mol-eq.), based on 4-oxo-γ-tocotrienol) was then introduced and the reaction mixture was further stirred for the time specified in Tables 1 and 2. The zinc was filtered off with a vacuum filter using Celite® (trade mark of Manville Corp., USA, for filter aids for separating and purifying liquids. Celite® consist of kieselguhr of differing grain sizes) and was rinsed with n-heptane (100 ml). The organic phase was washed, dried over $Na_2SO_4$, concentrated and the purity was determined by GC using area integration.

The crude product was purified in Examples 1 and 2 by flash chromatography using methyl t-butyl ether/heptane as eluent on silica gel, or by Kugelrohr distillation.

TABLE 1

|  | Example 1 | Example 2 | Example 3 | Example 4 |
| --- | --- | --- | --- | --- |
| 4-Oxo-γ-t. [g] | 1.0 | 5.0 | 10.3 | 10.0 |
| 4-Oxo-γ-t. [mmol] | 2.3 | 11.8 | 24.0 | 22.7 |
| Zn [mol-eq.] | 10 | 5 | 5 | 5 |
| Heptane [ml] | 10 | 80 | 100 | 100 |
| HCl (aq.) [ml] | 20 | 50 | 183 | 200 |
| HCl in aqueous solution [% by weight] | 20 | 20 | 22 | 24 |
| Temperature [° C.] | RT | 60 | 40 | 40 |
| Period [h] | 1.5 | 2 | 1 | 1 |
| Crude yield [g] | 0.96 | 4.64 | 9.88 | 9.27 |
| Purity [%] | 77 | — | 82 | 81 |
| Yield prior to purification [%] | 76 | — | 82 | 79 |
| Purification by | Flash chromatography | Kugelrohr distillation | — (*) | — |
| Yield after purification [%] | 63 | 52 | — | — |

Abbreviations used: t. = tocotrienol
aq. = aqueous solution
(*) Further reaction without purification in Example 12

TABLE 2

|  | Example 5 | Example 6 |
| --- | --- | --- |
| 4-Oxo-γ-t. [g] | 2.07 | 2.02 |
| 4-Oxo-γ-t. [mmol] | 4.83 | 4.71 |
| Zn [mol-eq.] | 5 | 5 |
| Solvent | Toluene | Octanoic acid |
| Amount of solvent [ml] | 20 | 20 |
| HCl (aq.) [ml] | 40 | 40 |
| HCl in aqueous solution [% by weight] | 22 | 22 |
| Temperature [° C.] | 40 | 40 |
| Period [h] | 1.0 | 3.0 |
| Crude yield [g] | 1.83 | 1.1 |
| Purity [%] | 82 | 62 |
| Yield prior to purification [%] | 76 | 38 |

Abbreviations used: t. = tocotrienol
aq. = aqueous solution

EXAMPLE 7

Preparation of γ-tocotrienol by reduction of 4-oxo-γ-tocotrienol in octane with Zn and an aqueous HCl solution with addition of dodecylamine as surface-active substance The experimental procedure was carried out in a similar manner to Examples 1 to 6, with addition of dodecylamine as surface-active substance and use of octane as solvent. Under the reaction conditions, the dodecylamine added is present as dodecylammonium chloride. In contrast to Examples 1 to 4, the reaction was carried out under ultrasound and not with stirring. Table 3 summarizes the reaction conditions and results.

TABLE 3

| | |
|---|---|
| 4-Oxo-γ-t. [g] | 0.83 |
| 4-Oxo-γ-t. [mmol] | 1.9 |
| Zn [mol-eq.] | 10 |
| Octane [ml] | 10 |
| HCl (aq.) [ml] | 30 |
| HCl in aqueous solution [% by weight] | 20 |
| Surface-active substance | Dodecylamine |
| Amount of surface-active substance [g] | 0.05 |
| Temperature [° C.] | 45 |
| Period [min] | 20 |
| Crude yield [g] | 0.77 |
| Purity [%] | 53 |
| Yield prior to purification [%] | 52 |

Abbreviations used: t. = tocotrienol
aq. = aqueous solution

EXAMPLE 8

Preparation of γ-tocotrienol by reduction of 4-oxo-γ-tocotrienol in heptane with Zn and an aqueous $H_2SO_4$ solution with addition of a surface-active compound The experimental procedure was carried out in a similar manner to Examples 1 to 6 using an aqueous $H_2SO_4$ solution (50% by weight, based on the aqueous solution) and with addition of a surface-active compound. Table 4 summarizes the reaction conditions and the results.

TABLE 4

| | |
|---|---|
| 4-Oxo-γ-t. [g] | 2.1 |
| 4-Oxo-γ-t. [mmol] | 4.7 |
| Zn [mol-eq.] | 8.5 |
| Heptane [ml] | 20 |
| $H_2SO_4$ (aq.) [ml] | 60 |
| $H_2SO_4$ in aqueous solution [% by weight] | 50 |
| Surface-active compound | Dodecylamine |
| Amount of surface-active compound [g] | 0.08 |
| Temperature [° C.] | 55 |
| Period [h] | 12 |
| Crude yield [g] | 1.5 |
| Conversion rate [%] | 98 |
| Selectivity [%] | 30 |

Abbreviations used: t. = tocotrienol
aq. = aqueous solution

EXAMPLE 9

Preparation of γ-tocotrienol by reduction of 4-oxo-γ-tocotrienol in heptane with Zn and an aqueous citric acid solution 4-Oxo-γ-tocotrienol (0.81 g, 1.9 mmol) was dissolved in n-heptane at 60° C. and an aqueous citric acid solution (20 ml, 40% by weight, based on the aqueous solution) was added with stirring. Zinc powder (1.3 g, 10 mol-eq., based on 4-oxo-γ-tocotrienol) was then added and the reaction mixture was stirred for 6 h at 60° C. and then for 2 h at 75° C. The zinc was filtered off via a vacuum filter using Celite, the organic phase was separated off, rinsed with water and dried over $Na_2SO_4$. The degree of conversion was determined to be 24% by gas chromatography (76% of 4-oxo-γ-tocotrienol was recovered). The selectivity of the reaction was 86%.

EXAMPLE 10

Preparation of γ-tocotrienol by reduction of 4-oxo-γ-tocotrienol in n-nonane with Zn and a mixture of an aqueous citric acid and HCl solution 4-Oxo-γ-tocotrienol (2.05 g, 4.78 mmol) was dissolved in hot (50° C.) nonane (35 ml) and heated to 100° C. with stirring together with an aqueous citric acid solution (300 ml, 40% by weight, based on the aqueous solution). In the course of 5 h, zinc powder was added with stirring a little at a time (3.1 g, 10 mol-eq., based on 4-oxo-γ-tocotrienol). An aqueous hydrochloric acid solution (30 ml, 24% by weight, based on the aqueous solution) was then added and in the course of 4 h, further zinc powder (3.1 g, 10 mol-eq.) was added a little at a time. After cooling to room temperature, the organic phase was separated off, washed with water, dried over $Na_2SO_4$ and concentrated. At complete conversion, a yield of 62% of γ-tocotrienol was determined by gas chromatography.

EXAMPLE 11

Preparation of γ-tocotrienol by reduction of 4-oxo-γ-tocotrienol with Zn and glacial acetic acid 4-Oxo-γ-tocotrienol (2.07 g, 4.83 mmol) was dissolved in 50 ml of glacial acetic acid and heated to reflux (approximately 80° C). 14.2 mol-eq. of zinc powder were introduced a little at a time and the mixture was stirred for 14 h under reflux. The progress of the reaction was followed by thin- and gas chromatography. At a conversion rate of 62% the reaction was terminated, residual zinc powder was filtered off and the filtrate was partitioned between heptane (100 ml) and water (100 ml). The heptane phase was washed with water, dried over $Na_2SO_4$ and concentrated. Chromatography on silica gel using methyl t-butyl ether/heptane as eluent gave 0.51 g (1.24 mmol) of γ-tocotrienol and 0.06 g of tocotrienol acetate. Unreacted 4-oxo-γ-tocotrienol (0.61 g) was recovered.

EXAMPLE 12

Preparation of γ-tocotrienol acetate by acetylation of γ-tocotrienol with acetic anhydride γ-Tocotrienol (crude product, prepared in accordance with Example 3, 4.8 g) was heated with 10 ml of acetic anhydride for 3.5 h under reflux and then freed from acetic acid and acetic anhydride under reduced pressure. Flash chromatography of the crude product with ethyl acetate/heptane as eluent on silica gel gave 3.7 g of γ-tocotrienol acetate.

EXAMPLES 13 and 14

Preparation of α-tocotrienol by reduction of 4-oxo-α-tocotrienol in toluene with zinc and an aqueous hydrochloric acid solution or in cyclohexane with zinc and an aqueous formic acid solution.

4-Oxo-α-tocotrienol (0.26 g, 0.6 mmol) was dissolved in toluene (Example 13) or cyclohexane (Example 14), at 40° C. The aqueous HCl solution (22% strength) (Example 13) or the aqueous formic acid solution (80% strength) (Example 14) was added with stirring. In the course of 8½ hours, zinc powder (13 or 15 molar equivalents, based on 4-oxo-α-tocotrienol) was then added and the reaction mixture was stirred for 5 hours at 40° C. and then for 7 hours at 65° C. The progress of the reaction is followed by sampling and thin layer chromatography. Unreacted zinc was filtered off with a vacuum filter using Celite and was rinsed with n-heptane. The organic phase was washed with water, dried over $Na_2SO_4$ and concentrated. Table 5 summarizes the reaction conditions and results.

TABLE 5

|  | Example 13 | Example 14 |
|---|---|---|
| 4-Oxo-α-T. [g] | 0.26 | 0.26 |
| 4-Oxo-α-T. [mmol] | 0.60 | 0.60 |
| Zinc [molar equivalents] | 13 | 15 |
| Solvent | Toluene | Cyclohexane |
| Solvent volume [ml] | 3 | 3 |
| Acid (aqueous) | Hydrochloric acid | Formic acid |
| Acid volume [ml] | 5 | 5 |
| Acid concentration in aqueous solution [% by weight] | 22% HCl | 80% HCOOH |
| Temperature [° C.] | 40 and 65 | 40 and 65 |
| Period (h) | 12 | 12 |
| Crude yield [g] | 0.10 | 0.10 |
| Conversion rate | 91% | 88% |
| Selectivity | 93% | 93% |

EXAMPLES 15 and 16

Preparation of δ-tocotrienol by reduction of 4-oxo-δ-tocotrienol in toluene with zinc and an aqueous hydrochloric acid solution or in cyclohexane with zinc and an aqueous formic acid solution 4-Oxo-δ-tocotrienol (0.20 g, 0.5 mmol) was dissolved by heating in toluene (Example 15) or cyclohexane (Example 16). The aqueous HCl solution (22% strength) (Example 15) or the aqueous formic acid solution (80% strength) (Example 16) was added with stirring. In the course of 0.5 hour (Example 15) or 7 hours (Example 16) zinc powder (6 or 10 molar equivalents, based on 4-oxo-δ-tocotrienol) was then added and the reaction mixture was stirred for 2 hours (Example 15) or 9 hours (Example 16) at 60° C. The zinc was filtered off with a vacuum filter using Celite and was rinsed with n-heptane. The organic phase was washed with water, dried over $Na_2SO_4$ and concentrated. Table 6 summarizes the reaction conditions and the results.

TABLE 6

|  | Example 15 | Example 16 |
|---|---|---|
| 4-Oxo-δ-T. [g] | 0.20 | 0.20 |
| 4-Oxo-δ-T. [mmol] | 0.50 | 0.50 |
| Zinc [molar equivalents] | 6 | 10 |
| Solvent | Toluene | Cyclohexane |
| Solvent volume [ml] | 3 | 3 |
| Acid (aqueous) | Hydrochloric acid | Formic acid |
| Acid volume (aqueous) [ml] | 5 | 5 |
| Acid concentration in aqueous solution [% by weight] | 22% HCl | 80% HCOOH |
| Temperature [° C.] | 60 | 60 |
| Period (h) | 2 | 9 |
| Crude yield [g] | 0.16 | 0.11 |
| Conversion rate | 100% | 99.5% |
| Selectivity | 93% | 56% |

EXAMPLE 17

Preparation of γ-tocotrienol by reduction of 4-oxo-γ-tocotrienol in cyclohexane with zinc and an aqueous formic acid solution.

4-Oxo-γ-tocotrienol (100.3 g, 0.24 mol) was dissolved in 500 ml of cyclohexane and 1 liter of formic acid (aqueous, 80% strength), at 65° C. In the course of 9½ hours, zinc powder (160 g, 2.45 mol) was added with stirring and the reaction mixture was stirred for 12 hours at 65° C. After a stirring time of 4 hours, a further 1 liter of formic acid (aqueous, 80% strength) was added. The organic phase was washed twice with water and then twice with a methanol/water mixture (1:1) and concentrated. Yield: 96.1 g of crude γ-tocotrienol. 91 g of the crude product were subjected to a molecular distillation at 200° C./<0.01 mbar and produced 86 g of γ-tocotrienol as a yellowish oil.

We claim:

1. A process for preparing chromanol derivatives of the formula I $$(I)$$

where
n is from 1 to 10,
$R^1$, $R^2$,
$R^3$, $R^4$ independently of one another are hydrogen or $C_1$–$C_4$ alkyl and
$R^5$ is hydrogen, $C_1$–$C_4$ alkyl, $C_6$–$C_{10}$ aryl, $C_7$–$C_{18}$ aralkyl, $C_7$–$C_{18}$ alkylaryl, $C_1$–$C_{22}$ acyl, or a group protecting the hydroxyl,
by reduction of the 4-oxochromanol derivatives of the formula II $$(II)$$

which comprises reacting the 4-oxochromanol derivatives of the formula II with metallic zinc in the presence of an acid or an acid mixture.

2. A process as claimed in claim 1, wherein an organic solvent is added to the reaction mixture.

3. A process as claimed in claim 1, wherein the reaction of the derivatives of the formula II with metallic zinc takes place in the presence of a hydrohalic acid or its aqueous solution.

4. A process as claimed in claim 1, wherein the reaction of the derivatives of the formula II with metallic zinc takes place in the presence of hydrochloric acid or its aqueous solution.

5. A process as claimed in claim 1, wherein the reaction of the derivatives of the formula II with metallic zinc takes place in the presence of a $C_1$–$C_{22}$-alkanecarboxylic acid and this is also used as organic solvent.

6. A process as claimed in claim 5, wherein the $C_1$–$C_{22}$-alkanecarboxylic acid is acetic acid.

7. A process for preparing chromanol esters of the formula Ia

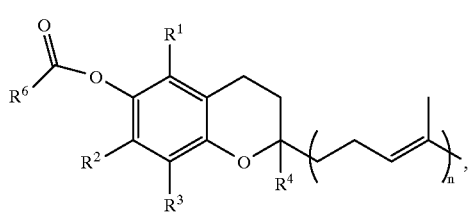

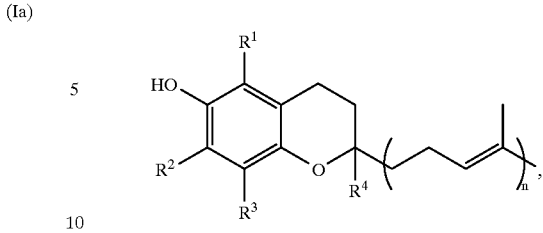

where n is from 1 to 10, $R^1$, $R^2$, $R^3$, $R^4$ independently of one another are hydrogen or $C_1$–$C_4$ alkyl and $R^6$ is hydrogen, $C_1$–$C_{21}$, alkyl or $C_2$–$C_{21}$ alkenyl, which comprises preparing the chromanol derivatives of the formula I where $R^5$=hydrogen (Ib) in accordance with a process of claim 1 and esterifying them by reacting them with an aliphatic $C_1$–$C_{22}$ carboxylic acid derivative of the formula III $$R^6\text{—COX} \quad (III),$$

where x is a leaving group which is displaced by the hydroxyl of the chromanol derivative of the formula Ib.

8. A process as claimed in claim 7, wherein the chromanol derivatives of the formula Ib are reacted with $C_1$–$C_{22}$ alkanecarboxylic acid which is present in the reaction mixture of the reduction step.

* * * * *